United States Patent
Wei et al.

(10) Patent No.: US 8,350,090 B1
(45) Date of Patent: Jan. 8, 2013

(54) PROCESSES FOR PREPARING CYCLOPENTENONES AND CYCLOPENTENONES FOR THE SYNTHESIS OF BENZINDENE PROSTAGLANDINS

(75) Inventors: Shih-Yi Wei, Yangmei (TW);
Wan-Chun Chang, Yangmei (TW);
Yu-Chih Yeh, Yangmei (TW)

(73) Assignee: Chirogate International Inc., Yangmei (TW)

( * ) Notice: Subject to any disclaimer, the term of this patent is extended or adjusted under 35 U.S.C. 154(b) by 0 days.

(21) Appl. No.: 13/216,321

(22) Filed: Aug. 24, 2011

(51) Int. Cl.
*C07C 45/00* (2006.01)
*C07C 49/00* (2006.01)

(52) U.S. Cl. .......... 568/319; 568/321; 568/330; 568/333

(58) Field of Classification Search .................. 568/319, 568/321, 330, 333
See application file for complete search history.

(56) References Cited

U.S. PATENT DOCUMENTS 7,626,024 B2 * 12/2009 Wei et al. ........................ 544/399
8,030,514 B2 * 10/2011 Wei et al. ........................ 560/122

OTHER PUBLICATIONS

Fujita et al. A new approach to cyclopentenones. Synthesis, 1983, vol. 12, 997-1000; HCAPLUS abstract; Document No. 100:102782.*

Yoshida et al. Radical Addition Reactions to Allylstannanes Having Substituents at C-1. Highly Efficient Synthesis of Enantiomerically Pure Alpha-Alkylcyclopentenones, the Key Component for Synthesis of Prostaglandins by the Two-Component Coupling Process. Journal of Organic Chemistry, 1994, vol. 59, 6153-6155.*

* cited by examiner

*Primary Examiner* — Sikarl Witherspoon
(74) *Attorney, Agent, or Firm* — Ladas & Parry LLP

(57) ABSTRACT

The present invention provides novel processes of preparing racemic and optically active cyclopentenones of Formula I:

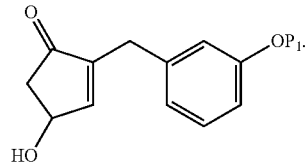

The invention also provides novel cyclopentenones of formula I in racemic or optically active form.

23 Claims, No Drawings

PROCESSES FOR PREPARING CYCLOPENTENONES AND CYCLOPENTENONES FOR THE SYNTHESIS OF BENZINDENE PROSTAGLANDINS

BACKGROUND OF THE INVENTION

1. Field of the Invention

The present invention relates to novel processes for preparing cyclopentenones of Formula I,

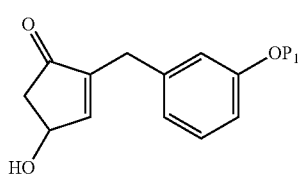

which are useful for the preparation of the corresponding benzindene Prostaglandins. The invention also relates to novel cyclopentenones prepared from the processes.

2. Description of the Prior Art

Benzindene prostaglandins are known to be useful to treat a variety of conditions. Cyclopentenones of Formula I

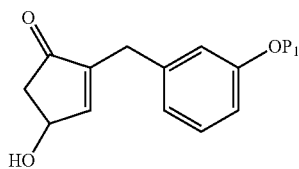

wherein $P_1$ is a protecting group for the phenol group, which are also disclosed in the co-pending patent application filed on the even date and entitled "INTERMEDIATES FOR THE SYNTHESIS OF BENZINDENE PROSTAGLANDINS AND PREPARATIONS THEREOF," are key intermediates for the synthesis of benzindene Prostaglandins. Racemic or optically active cyclopentenones of Formula I were not disclosed in the prior art. As shown in the following Scheme 1, Sato disclosed in *J. Org. Chem.*, 59, 21, 6153 (1994) optically active cyclopentenones of Formula B and a process for preparing the same:

Scheme 1

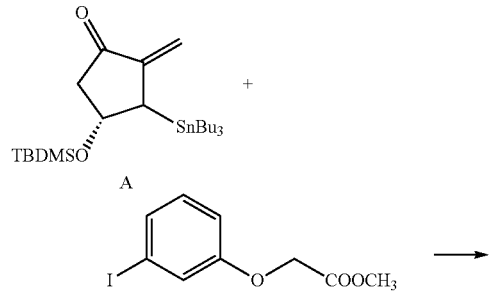

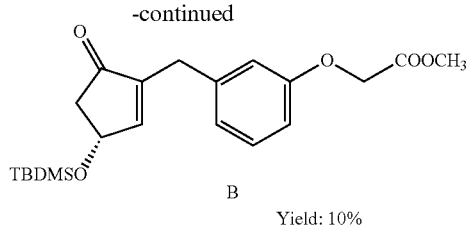

Yield: 10%

However, this preparation process yielded as low as 10%. Moreover, the starting material of Formula A used in this preparation is costly and not easy to obtain as it normally would be obtained from a 11-step synthesis process starting with the expensive D-erythro-Pent-1-ental of Formula C as shown in the following Scheme 2 [*J. Org. Chem.*, 53, 23, 5590 (1994); JP 07252276].

Scheme 2

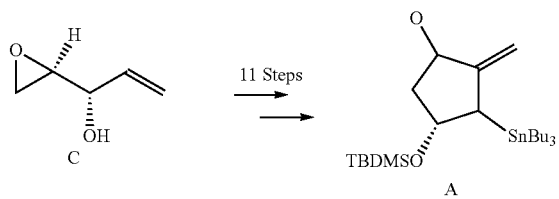

There has been a demand for a process for the preparation of the cyclopentenones of Formula I that involves less steps and is more convenient to operate.

SUMMARY OF THE INVENTION

The present invention provides novel processes of preparing racemic and optically active cyclopentenones of Formula I.

The invention also provides novel cyclopentenones of formula I in racemic or optically active form.

DETAILED DESCRIPTION OF THE INVENTION

According to the present invention and as shown in the following Scheme A, cyclopentenones of Formula I

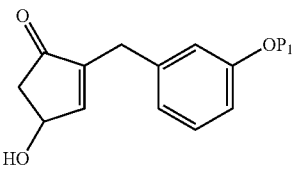

wherein $P_1$ is a protecting group for the phenol group are prepared from a protected 2-(3-hydroxyphenyl)acetic acid of Formula V. Suitable protecting groups for the phenol group are preferably acid stable, and include, but are not limited to, a $C_{1-8}$alkyl, allyl, unsubstituted or substituted benzyl, acetyl, $C_{1-8}$ alkylcarbonyl, methoxymethyl, methoxythiomethyl, 2-methoxyethoxymethyl, bis(2-chloroethoxy)methyl, tetrahydropyranyl, tetrahydrothiopyranyl, 4-methoxytetrahydropyranyl, 4-methoxytetrahydrothiopyranyl, tetrahydrofuranyl, tetrahydrothiofuranyl, 1-ethoxyethyl, 1-methyl-1-methoxyethyl, triphenylmethyl, and $SiR_aR_bR_c$ wherein $R_a$, $R_b$ and $R_c$ are each independently a $C_{1-8}$ alkyl, phenyl, benzyl, a substituted phenyl, or a substituted benzyl, wherein when a defined radical is substituted, the substituent is selected from the group consisting of halogen, alkyl, aryl, alkoxyl, aryloxy, thioalkoxy, thioaryloxy, alkylamino, arylamino, cyano, alkoxycarbonyl, arylcarbonyl, arylaminocarbonyl, alkylaminocarbonyl, and nitro. Preferably, the protecting group is an unsubstituted or substituted benzyl; the group of $SiR_aR_bR_c$, particularly, wherein $R_a$, $R_b$ and $R_c$ are each independently a $C_{1-8}$ alkyl; a $C_{1-8}$ alkyl; acetyl; or $C_{1-8}$ alkylcarbonyl.

Scheme A

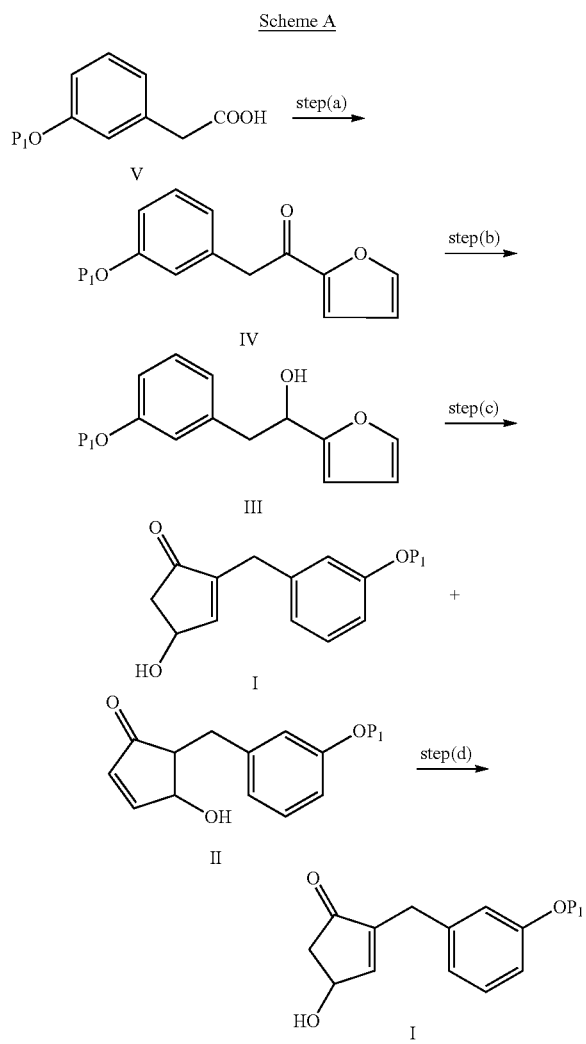

In Scheme A, Step (a) is a Friedel-Crafts acylation. In Step (a), furan and an acyl donor of the acid compound of Formula V undergo a Friedel-Crafts acylation to obtain a 2-acylfuran of Formula IV. For example, Step (a) includes mixing a protected 2-(3-hydroxyphenenyl)acetic acid of Formula V with furan in a suitable solvent, adding an anhydride, and reacting the mixture optionally in the presence of a catalyst to obtain the 2-acylfuran of Formula IV. The solvent suitable for the reaction of Step (a) is preferably dichloromethane, chloroform, tetrahedrofuran, or toluene or a mixture thereof; and the suitable anhydride can be chloroacetic anhydride or trifluoroacetic anhydride or a mixture thereof. If present, the catalyst can be a Lewis acid such as boron trifluoride, trifluoroacetic acid, tin(IV) chloride, or zinc chloride.

Step (b) of Scheme A comprises reducing a 2-acylfuran of Formula IV with a reducing agent in a suitable solvent to form a furancarbinol of Formula III. According to the present invention, the reducing agent is selected from $NaBH_4$, $LiBH_4$, $Zn(BH_4)_2$, $Me_4NBH(OAc)_3$, $NaBH_3CN$, $LiBH(s\text{-}Bu)_3$, $NaBH(s\text{-}Bu)_3$, $KBH(s\text{-}Bu)_3$, $LiBHEt_3$, $LiAlH_4$, (iso-$Bu)_2$AlH, $LiAlH(t\text{-}BuO)_3$, or $NaAlH_2(OCH_2CH_2OCH_3)_2$, or a mixture thereof. Preferably, the reducing agent is $NaBH_4$, $LiBH_4$, $LiAlH_4$, or (iso-$Bu)_2$AlH or a mixture thereof. More preferably, the reducing agent is $NaBH_4$ Step (c) of Scheme A is a transformation (i.e., rearrangement) reaction, which can be carried out in an aqueous medium containing 100% water or water mixed with a small amount of an organic solvent. The pH of the reaction is maintained in the range of from about 2.5 to about 6.5 with an organic or inorganic acidic or basic substance, preferably with a buffer solution of dipotassium hydrogen phosphate/phosphoric acid. The rearrangement reaction is preferably conducted at a temperature in the range from about 60° C. to about 200° C., more preferably from about 80° C. and 140° C.

In one embodiment, a mixture of cyclopentenones of Formulae II and I, generated from the rearrangement reaction of Step (c), is directly subjected to Step (d) without further purification. Step (d) is an isomerization reaction, which can be conducted in the presence of chloral hydrate and triethylamine. By the isomerization reaction, the cyclopentenones of Formula II are isomerized into the cyclopentenones of Formula I. The resultant crude cyclopentenones of Formula I are racemic.

The present invention further provides a process for preparing optically active cyclopentenones of Formula I.

According to one embodiment of the present invention, the process for preparing a compound of Formula I enriched in the (R)-enantiomer and having an optical purity of at least 95% enantiomeric excess

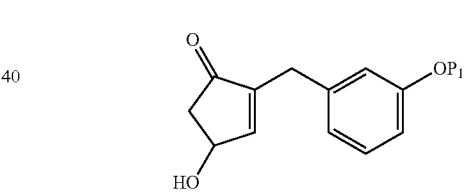

wherein $P_1$ is as defined hereinbefore, comprising the steps of:
(e) enantioselectively (R)-esterifying the racemic alcohol mixture of the compound of Formula I with an acyl donor and a first lipase;
(f) removing the unreacted (S)-alcohol or converting the unreacted (S)-alcohol into a corresponding (R)-ester; and
(g) deacylating the resultant (R)-ester.

As shown in Step (e) of Scheme B, racemic cyclopentenones of Formula I are reacted with an acyl donor of Formula D,

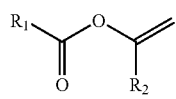

wherein $R_1$ and $R_2$ are independently a C1~C6 lower alkyl or H, in the presence of an enantioselective lipase, wherein the acyl donor preferentially reacts with the cyclopentenones in (R)-form, thereby generating a mixture consisting of the optically active esters of Formula (R)-VIII and the unreacted alcohols of Formula (S)-I

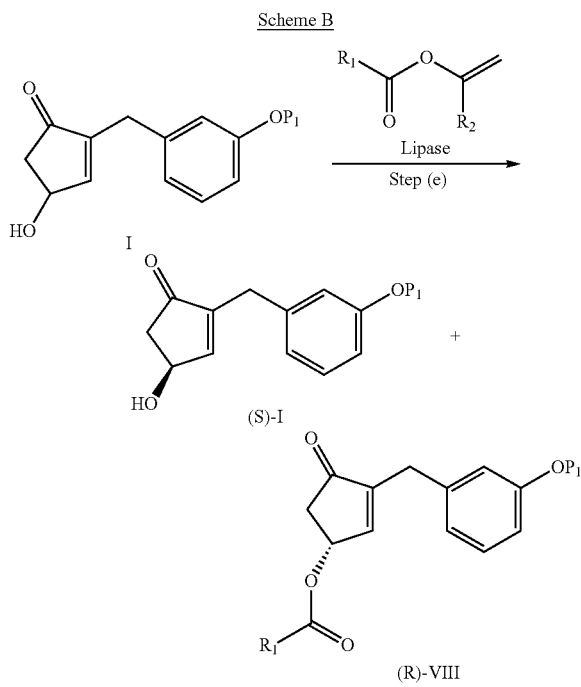

According to the invention, the resultant esters of Formula (R)-VIII possess an optical activity of at least 85% e.e., preferably at least 90% e.e., more preferably at least 95% e.e and most preferably up to 99% e.e.

In one embodiment, the enantioselective lipase used in the invention is derived from a pig liver, a porcine pancrease, or microorganisms, e.g., *Achromobacter* spp., *Alcaligenes* spp., *Aspergillus tiger*, *Candida antarcitica*, *Candida rugosa*, *Candida lypolytica*, *Chromobacterium viscosum*, *Mucor janvanicus*, *Mucor miehei*, *Penicillum Camenberti*, *Penicillium roqueforteii*, *Pseudomonas cepacia*, *Pseudomonas fluorescence*, *Pseudomonas* spp., *Pseudomonas stutzri*, *Rhizopus Delmar*, *Rhizopus Niveus*, *Rhizopus oryze*, and *Rhizopus* spp. More preferably, the enantioselective lipase is derived from *Achromobacter spp*, *Alcaligenese* spp., *Candida antarcitica*, *Pseudomonas fluorescens*, *Pseudomonas stutzri*, or *Pseudomonas cepacia*.

According to the embodiments of the present invention, the acyl donor can be vinyl acetate, isopropenyl acetate, vinyl valerate, isopropenyl valerate, vinyl butyrate, or isopropenyl butyrate or a mixture thereof.

The enantioselective esterification may be performed in an organic solvent, which can be selected from hexane, cyclohexane, toluene, tetrahydrofuran, methyl ethyl ketone, methyl isobutyl ketone, ethyl ether, isopropyl ether, methyl isopropyl ether, or tert-butyl methyl ether or a mixture thereof.

The lipase may be present in the process of the invention in any form, including a purified form, or a crude form, or a natural form associated with the microorganism per se from which the lipase is derived, as long as its optical selectivity in the esterification is maintained. The chemical stability, activity, or enantioselectivity of the lipase can be further enhanced by gene modification, DNA recombination, or immobilization.

The amount of the lipase used varies with many factors such as the activity of the lipase, the amount of the reactants, or the solvent used. In one embodiment of the present invention, the lipase is used in an amount ranging from 0.01 mass equivalents to 10 mass equivalents per mass equivalent of the cyclopentenone of Formula I.

The reaction mixture should be constantly stirred, shaked, or ultrasounded to ensure a good contact between the reactants and the lipase. Further, the temperature suitable for the reaction is between 5° C. and 50° C., and the reaction can be conducted at ambient temperature. The enantiomerically selective esterification can be stopped by removing the lipase from the reaction mixture when an appropriate conversion of the starting material is obtained. In one embodiment, the lipase is removed to stop the enzymatic esterification when a conversion rate of between 30% to 70%, more preferably of approximately 50% is achieved.

The ester of Formula (R)-VIII and the unreacted alcohol (S)-1 in the reaction mixture from step (f) can be directly separated. Since the structures and the properties of the esters of Formula (R)-VIII are distinctively different from those of the alcohols of Formula (S)-1, the esters of Formula (R)-VIII can be easily isolated from the mixture by any suitable conventional method, such as flash chromatography on silica gel:

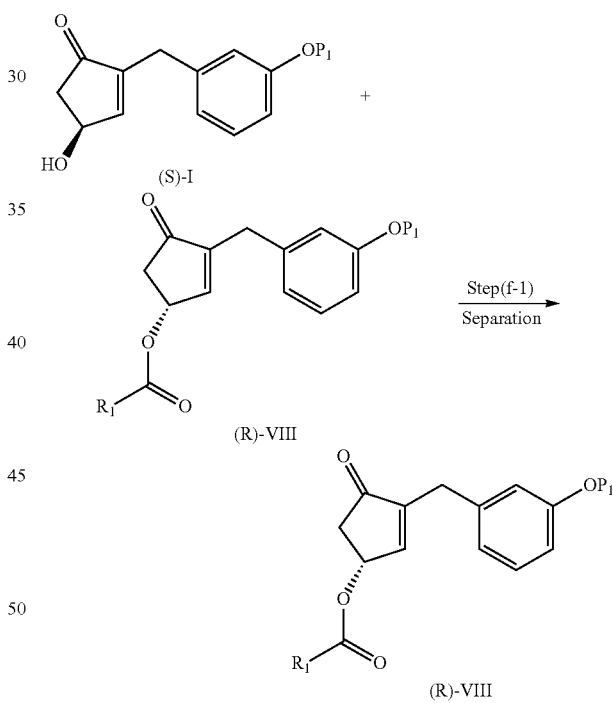

Alternatively, according to one embodiment of the present invention and as shown in the following scheme, the unreacted alcohols (S)-I are converted into the corresponding esters of Formula (R)-VIII' by conversion of the OH group into an acyloxy group with an acyloxy donor of Formula $R_3COOH$, wherein $R_3$ is as defined for $R_1$, in the presence of a dialkylazodicarboxylate, such as diethylazodicarboxylate, diisopropylazodicarboxylate, or dibenzylazodicarboxylate, or a mixture thereof and a triarylphosphine, such as triphenylphosphine, in a suitable solvent, such as toluene. In Step (f-2), almost 100% of the alcohols of Formula (S)-1 in the mixture are converted to the esters of Formula (R)-VIII'.

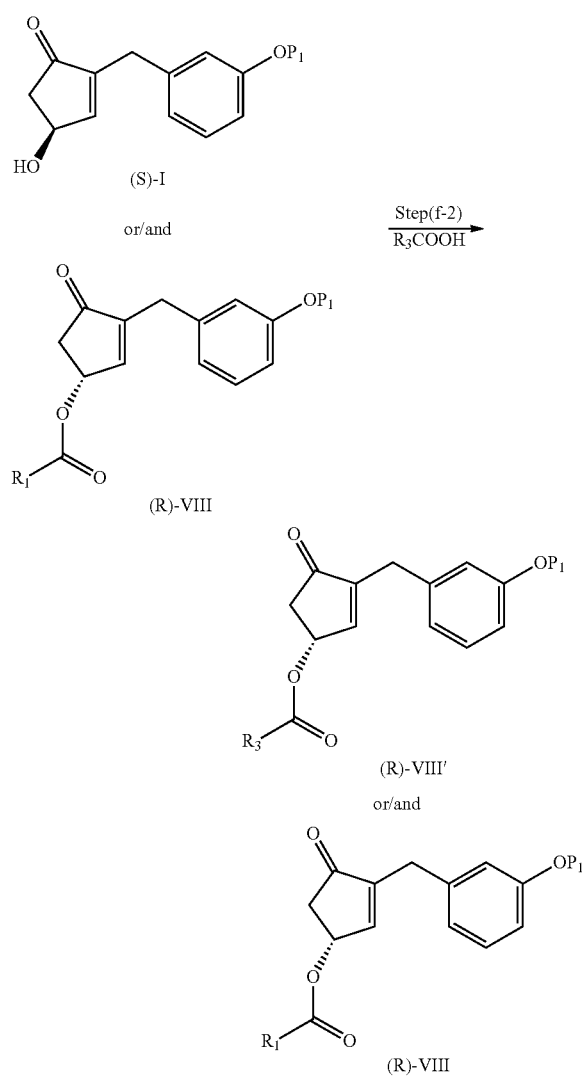

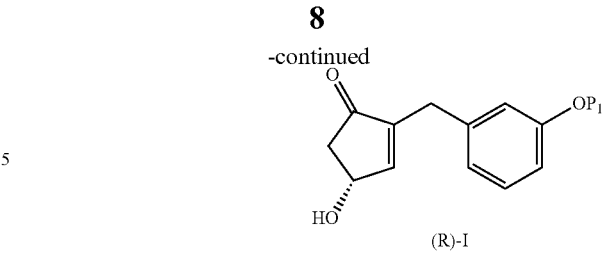

In one embodiment of the invention, the deacylation reaction is a chemical hydrolysis, either an acidic hydrolysis or a basic hydrolysis. If the hydrolysis is an acidic hydrolysis, it is performed in the presence of an alcohol and an acid catalyst such as phosphoric acid, p-toluenesulfonic acid, hydrobromic acid, hydrochloric acid, nitric acid or sulfuric acid or a mixture thereof, for the cleavage of the esters of (R)-VIII or/and (R)-VIII' to obtain the cyclopentenones of Formula (R)-1. For example, the acidic hydrolysis is performed in the presence of sulfuric acid and methanol or ethanol. If the hydrolysis is a basic hydrolysis, it is performed in the presence of a base such as LiOH, NaOH or KOH or a mixture thereof.

In another embodiment of the invention, the deacylation reaction in Step (e) is an enzymatic cleavage reaction. The enzymatic cleavage reaction is either a hydrolysis or an alcoholysis and can be performed in the presence of water, a buffer, a water- or buffer-saturated organic solvent, or an alcohol containing aqueous or non-aqueous system. In addition, the reaction system for the enzymatic deacylation can be a homogenous or two-phase system containing water or a buffer and a water-insoluble solvent. The esters should be either dissolved or finely dispersed in the reaction system so as to be in a good contact with the lipase therein. If necessary, a phase transfer catalyst, e.g., a salt or a surfactant, can be added to the system to increase the reaction rate. Suitable organic solvents can be those immiscible with water or those saturated with water or a buffer, or water-miscible organic solvents, such as alcohols. Suitable buffers include, but are not limited to, those prepared from a halide, a carbonate, a phosphate, a sulfate, a nitrate, a bicarbonate, and/or an acetate and are preferably at a pH ranging from 5 to 8. Suitable organic solvents used in the reaction can be water-miscible solvents, which include but are not limited to, alkyl alcohols, aryl alcohols, alkenyl alcohols, methyl sulfoxide, acetone, dimethyl formamide, acetonitrile, and a mixture thereof, or water-immiscible solvents, which include but are not limited to, hexane, toluene, ether, petroleum ether, isopropyl ether, methyl tert-butyl ether, tetrahydrofuran, methyl ethyl ketone, methyl isobutyl ketone, dioxane, and a mixture thereof.

The enzyme employed is a lipase suitable for the hydrolysis of the esters. Preferably, the lipase used in Step (e) is derived from *Candida antarcitica, Achromobacter* spp., *Alcaligenese* spp., *Psudomonas* spp, *Pseudomonas fluorescens, Pseudomonas stutzri*, or *Pseudomonas cepacia*. More preferably, the lipase is derived from *Candida antarcitica, Psudomonas* spp., or *Achmmobacter* spp., and most preferably from *Candida antarcitica*.

The reaction is monitored by HPLC using a chiral column and stopped by removing the lipase, preferably when the conversion rate reaches about 90%. Optionally, the unreacted esters of (R)-VIII and/or (R)-VIII' can be removed after the deacylation. According to the invention, alcohols of Formula (R)-1 are produced with an optical activity of at least 95% e.e., preferably at least 98%, more preferably at least 99%, and most preferably at least 99.9 e.e.

The present invention further provides a racemic or an optically active compound of Formula I For the purpose of obtaining optically active cyclopentenones of Formula (S)-I of the invention, it is not necessary to isolate the esters of Formula (R)-VIII or remove the alcohols of Formula (S)-I from the mixture obtained in Step (e). Instead, the mixture can be directly subjected to the inversion reaction of Step (f-2) to obtain a mixture of the esters of Formula (R)-VIII and (R)-VIII'.

As shown in the following scheme, the esters of Formula (R)-VIII or/and (R)-VIII' are further subjected to a deacylation reaction in Step (g).

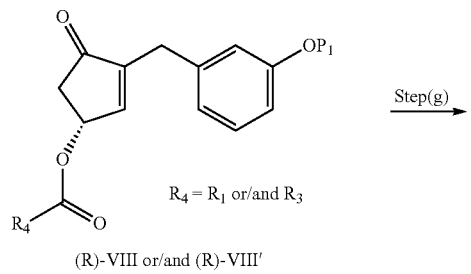

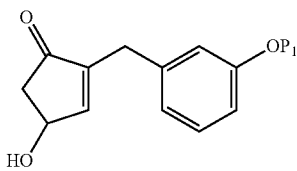

wherein R₁ is a protecting group for the phenol group and is selected from the group consisting of a $C_{1-8}$ alkyl, allyl, unsubstituted or substituted benzyl, acetyl, $C_{1-8}$ alkylcarbonyl, methoxymethyl, methoxythiomethyl, 2-methoxyethoxymethyl, bis(2-chloroethoxy)methyl, tetrahydropyranyl, tetrahydrothiopyranyl, 4-methoxytetrahydropyranyl, 4-methoxytetrahydrothiopyranyl, tetrahydrofuranyl, tetrahydrothiofuranyl, 1-ethoxyethyl, 1-methyl-1-methoxyethyl, triphenylmethyl, and $SiR_aR_bR_c$ wherein $R_a$, $R_b$ and $R_c$ are each independently a $C_{1-8}$ alkyl, phenyl, benzyl, a substituted phenyl, or a substituted benzyl, wherein when a defined radical is substituted, the substituent is selected from the group consisting of halogen, alkyl, aryl, alkoxyl, aryloxy, thioalkoxyl, thioaryloxy, alkylamino, arylamino, cyano, alkoxycarbonyl, arylcarbonyl, arylaminocarbonyl, alkylaminocarbonyl, and nitro. Preferably, the protecting group is an unsubstituted or substituted benzyl; the group of $SiR_aR_bR_c$, wherein $R_a$, $R_b$ and $R_c$ are each independently a $C_{1-8}$ alkyl; a $C_{1-8}$ alkyl; acetyl; or a $C_{1-8}$ alkylcarbonyl.

According to an embodiment of the present invention; the compound of Formula I is enriched in the (R)-enantiomer and having an optical purity of at least 95%, preferably at least 98%, more preferably at least 99%, and most preferably at least 99.9 enantiomeric excess.

The following examples are used to further illustrate the present invention, but not intended to limit the scope of the present invention. Any modifications or alterations that can be easily accomplished by persons skilled in the art fall within the scope of the disclosure of the specification and the appended claims.

EXAMPLE 1

1-(Furan-2-yl)-2-(3-methoxyphenyl)ethan-1-one

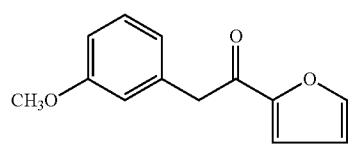

3-Methoxyphenylacetic acid (20 g, 120.35 mmol) was dissolved in $CH_2Cl_2$ (200 mL), and furan (24.6 g, 361.39 mmol) and trifluoroacetic anhydride (37.8 g, 180 mmol) were added to the solution. The reaction was kept being stirred overnight at room temperature. The reaction was quenched with saturated $NaHCO_3$ to pH=6.9, and the organic reagent in the mixture was evaporated. The residue was extracted with EtOAc, and the organic layer was washed with brine, dried over $MgSO_4$, and evaporated. The resulting residue was purified by chromatography on a silica gel column using hexane-EtOAc as eluent to give 1-(furan-2-yl)-2-(3-methoxyphenyl)ethan-1-one as yellow oil: 20 g (yield: 77%)

¹H NMR (300 MHz, CDCl₃) δ 3.76 (3H, s), 4.07 (2H, s), 6.50 (1H, dd, J=1.7, 3.6 Hz), 6.76-6.89 (3H, m), 7.19-7.26 (2H, m), 7.57 (1H, dd, J=0.7, 1.7 Hz).

EXAMPLE 2

1-(Furan-2-yl)-2-(3-benzyloxyphenyl)ethan-1-one

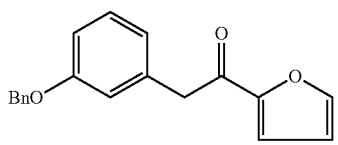 [SMILES: O=C(Cc1cccc(OCc2ccccc2)c1)c1ccco1]

3-Benzyloxyphenylacetic acid (3.5 kg, 14.45 mol) was dissolved in $CH_2Cl_2$ (35 L), and furan (3.0 kg, 44 mol) and trifluoroacetic anhydride (4.55 kg, 21.65 mol) were added to the solution. The reaction was kept being stirred at room temperature for 2 days. The reaction was quenched with saturated $NaHCO_3$ to pH=6.9, and the organic reagent in the mixture was evaporated. The residue was extracted with EtOAc, and the organic layer was washed with brine, dried over $MgSO_4$, and evaporated. The resulting residue was purified by chromatography on a silica gel column using hexane-EtOAc as eluent to give the 1-(furan-2-yl)-2-(3-benzyloxyphenyl)ethan-1-one as yellow oil: 4 kg (yield: 95%)

¹H NMR (300 MHz, CDCl₃) δ 4.08 (2H, s), 5.03 (2H, s), 6.50 (1H, dd, J=1.71, 3.59 Hz), 6.86-6.97 (3H, m), 7.19-7.44 (7H, m), 7.51 (1H, dd, J=0.76, 1.7 Hz)

¹³C NMR (75 MHz, CDCl₃) δ 45.3, 69.8, 112.3, 113.3, 115.9, 118.0, 122.0, 127.4, 127.9, 128.5, 129.6, 135.5, 136.8, 146.6, 152.2, 158.9, 186.3

EXAMPLE 3

1-(Furan-2-yl)-2-(3-methoxyphenyl)ethan-1-ol

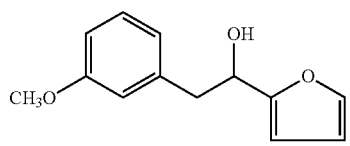

1-(Furan-2-yl)-2-(3-methoxyphenyl)ethan-1-one (20 g, 92.56 mmol) was dissolved in MeOH (200 mL), and $NaBH_4$ (3.5 g, 92.52 mmol) was slowly added to the solution at 5° C. After the reaction was completed, the solution was quenched with $H_2O$, and the MeOH was evaporated. The residue was extracted with EtOAc and the organic layer was washed with brine, dried over $MgSO_4$, and evaporated to give the 1-(furan-2-yl)-2-(3-methoxyphenyl)ethan-1-ol as yellow oil: 20 g (crude yield: 98%)

¹H NMR (300 MHz, CDCl₃) δ 2.12 (1H, s), 3.15 (2H, m), 3.79 (3H, s), 4.93 (1H, s), 6.25 (1H, s), 6.35 (1H, s), 6.74 (1H, m), 6.81 (2H, m), 7.23 (1H, t, J=7.9 Hz), 7.43 (1H, s)

EXAMPLE 4

1-(Furan-2-yl)-2-(3-benzyloxyphenyl)ethan-1-ol

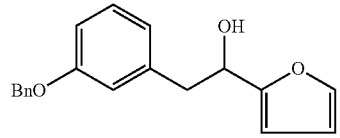 [SMILES: OC(Cc1cccc(OCc2ccccc2)c1)c1ccco1]

1-(Furan-2-yl)-2-(3-benzyloxyphenyl)ethan-1-one (4 kg, 13.69 mol) was dissolved in MeOH (35 L), and NaBH$_4$ (520 g, 13.75 mol) was slowly added to the solution at 5° C. After the reaction was completed, the solution was quenched with H$_2$O, and the MeOH was evaporated. The residue was extracted with EtOAc and the organic layer was washed with brine, dried over MgSO$_4$, and evaporated to give the 1-(furan-2-yl)-2-(3-benzyloxyphenyl)ethan-1-ol as yellow oil: 3.97 kg (crude yield: 98%)

$^1$H NMR (300 MHz, CDCl$_3$) δ 2.07 (1H, br), 3.13 (2H, m), 4.92 (1H, dd, J=5.47, 7.94 Hz), 5.04 (2H, s), 6.23 (1H, d, J=3.23 Hz), 6.34 (1H, dd, J=1.82, 3.22 Hz), 6.80-6.89 (3H, m), 7.23 (1H, t, J=7.89 Hz), 7.31-7.46 (6H, m)

$^{13}$C NMR (75 MHz, CDCl$_3$) δ2.2, 68.6, 69.9, 106.4, 110.2, 113.1, 115.9, 122.0, 127.5, 127.9, 128.5, 129.5, 136.9, 138.9, 141.9, 155.6, 158.9

EXAMPLE 5

4-Hydroxy-2-(3-Methoxybenzyl)cyclopent-2-enone and 4-Hydroxy-5-(3-Methoxybenzyl)cyclopent-2-enone

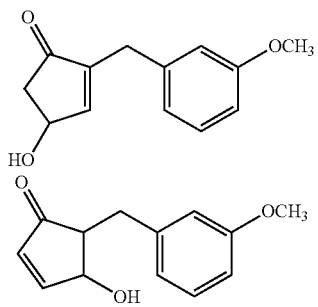

1-(Furan-2-yl)-2-(3-methoxyphenyl)ethan-1-ol (20 g, 91.7 mmol) and KH$_2$PO$_4$ (0.4 g, 0.02 mmol) was added to H$_2$O (400 mL) and H$_3$PO$_4$ was added until pH=3.0. The reaction was kept being stirred at 120° C. overnight. After being cooled, NaCl (300 g) was added, and the reaction was extracted with EtOAc, dried over MgSO$_4$, and evaporated to give the crude 4-Hydroxy-2-(3-methoxybenzyl)cyclopent-2-enone and 4-Hydroxy-5-(3-methoxybenzyl)cyclopent-2-enone as black oil: 19 g (crude yield: 95%).

EXAMPLE 6

4-Hydroxy-2-(3-Benzyloxybenzyl)cyclopent-2-enone and 4-Hydroxy-5-(3-Benzyloxybenzyl)cyclopent-2-enone

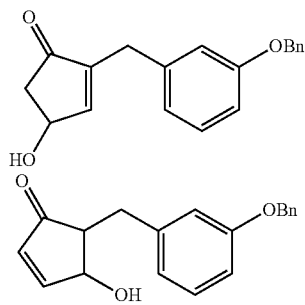

1-(Furan-2-yl)-2-(3-benzyloxyphenyl)ethan-1-ol (3.97 kg, 13.49 mol) and KH$_2$PO$_4$ (120 g, 0.88 mol) was added to H$_2$O (120 L) and H$_3$PO$_4$ was added until pH=3. The reaction was kept being stirred at 120° C. for 5 hours. After being cooled, NaCl (25 kg) was added, and the reaction was extracted with EtOAc, dried over MgSO$_4$, and evaporated to give the crude 4-hydroxy-2-(3-benzyloxybenzyl)cyclopent-2-enone and 4-hydroxy-5-(3-benzyloxybenzyl)cyclopent-2-enone as black oil: 3.4 kg (crude yield: 85%).

EXAMPLE 7

2-(3-Methoxybenzyl)-4-hydroxycyclopent-2-enone

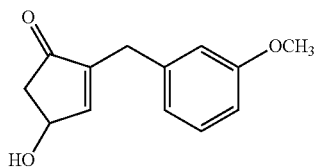

Crude 4-Hydroxy-2-(3-methoxybenzyl)cyclopent-2-enone and 4-Hydroxy-5-(3-methoxybenzyl)cyclopent-2-enone (19 g, 87.12 mmol) was dissolved in PhCH$_3$ (100 mL), and chloral hydrate (0.6 g, 4.11 mmol) and Et$_3$N (5.6 g, 55.34 mmol) were added to the solution, and the mixture was stirred at room temperature overnight. The reaction was evaporated. The resulting residue was purified by chromatography on a silica gel column using hexane-EtOAc as eluent to give 4-hydroxy-2-(3-methoxybenzyl)cyclopent-2-enone as brown oil: 15.32 g (yield: 81%).

$^1$H NMR (300 MHz, CDCl$_3$) δ 2.317 (1H, br), 2.324 (1H, dd, J=2.0, 18.6 Hz), 2.83 (1H, dd, J=6.0, 18.6), 3.48 (2H, s), 3.78 (3H, s), 4.90 (1H, m), 6.73-6.79 (3H, m), 67.0 (1H, m), 7.21 (1H, J=7.9)

EXAMPLE 8

4-Hydroxy-2-(3-Benzyloxybenzyl)cyclopent-2-enone

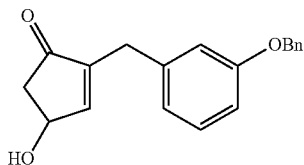 [SMILES: O=C1CC(O)C=C1Cc1cccc(OCc2ccccc2)c1]

Crude 4-hydroxy-2-(3-Benzyloxybenzyl)cyclopent-2-enone and 4-hydroxy-5-(3-Benzyloxybenzyl)cyclopent-2-enone (3.4 kg, 15.6 mol) was dissolved in PhCH$_3$ (20 L), and chloral (91 g, 0.62 mol) and Et$_3$N (827 g, 8.17 mol) were added to the solution, and the mixture was stirred at room temperature for 4 hours. The reaction was evaporated. The resulting residue was purified by chromatography on a silica gel column using hexane-EtOAc as eluent to give 4-hydroxy-2-(3-benzyloxybenzyl)cyclopent-2-enone as brown oil: 2.1 kg (yield: 62%).

$^1$H NMR (500 MHz, CDCl$_3$) δ 2.29 (1H, br), 2.30 (1H, dd, J=2, 19 Hz), 2.8 (1H, dd, J=6, 18.5 Hz), 3.46 (2H, ab), 4.84-4.87 (1H, m), 5.04 (2H, s), 6.19-6.81 (2H, m), 6.85 (1H, dd, J=2, 8.5 Hz) 6.96 (1H, m), 7.22 (1H, t, J=8 Hz), 7.33 (1H, m), 7.40 (4H, m)

$^{13}$C NMR (125 MHz, CDCl$_3$) δ 30.9, 44.7, 68.3, 69.9, 112.7, 115.6, 121.6, 127.5, 127.9, 128.5, 129.6, 136.8, 139.4, 147.1, 157.3, 158.9, 205.6

EXAMPLE 9

(R)-3-(3-Methoxybenzyl)-4-oxocyclopent-2-enyl acetate

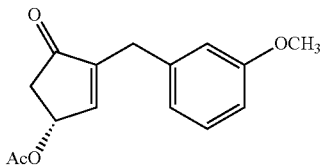 [SMILES: COc1cccc(CC2=C[C@H](OC(C)=O)CC2=O)c1]

4-Hydroxy-2-(3-methoxybenzyl)cyclopent-2-enone (9 g, 41.26 mmol) was dissolved in isobutyl methyl ketone (90 mL), and vinyl acetate (8.4 g, 97.57 mmol) and Lipase derived from *Alcaligenese* spp. (0.9 g) were added to the solution, and the mixture was stirred at room temperature overnight. The reaction mixture was filtered to remove Lipase and the filtrate was evaporated. The resulting residue was purified by chromatography on a silica gel column using hexane-EtOAc as eluent to give (R)-3-(3-methoxybenzyl)-4-oxocyclopent-2-enyl acetate as yellow oil: 4.29 g (95% ee by HPLC using a chiral column) and (S)-4-hydroxy-2-(3-methoxybenzyl)cyclopent-2-enone as yellow oil: 4.05 g (100% ee by HPLC using a chiral column)

$^1$H NMR (300 MHz, CDCl$_3$) δ 2.04 (3H, s), 2.38 (1H, dd, J=2, 18.8 Hz), 2.88 (1H, dd, J=6.3, 18.9 Hz), 3.48 (2H, s), 3.78 (3H, s), 5.73 (1H, m), 6.72-6.78 (3H, m), 6.99 (1H, m), 7.21 (1H, t, J=8.1 Hz)

EXAMPLE 10

(R)-3-(3-Methoxybenzyl)-4-oxocyclopent-2-enyl acetate

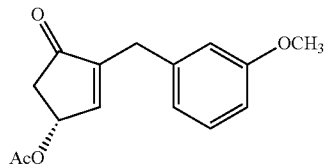 [SMILES: COc1cccc(CC2=C[C@H](OC(C)=O)CC2=O)c1]

4-Hydroxy-2-(3-methoxybenzyl)cyclopent-2-enone (9 g, 41.26 mmol) was dissolved in isobutyl methyl ketone (90 mL), and vinyl acetate (8.4 g, 97.57 mmol) and Lipase derived from *Pseudomonas cepacia* (0.9 g) were added to the solution, and the mixture was stirred at room temperature overnight. The reaction mixture was filtered to remove the Lipase and the filtrate was evaporated. The resulting residue was dissolved in PhCH$_3$ (150 ml), and triphenylphosphine (6.5 g; 24.78 mmol) and AcOH (1.61 g, 26.81 mmol) were added to the solution. Then diisopropylazodicarboxylate (5 g, 24.72 mmol) was added to the mixture at 5° C. After the reaction was completed, the reaction mixture was filtered to remove the precipitate and the filtrate was evaporated. The residue was purified by chromatography on a silica gel column using hexane-EtOAc as eluent to give the (R)-3-(3-methoxybenzyl)-4-oxocyclopent-2-enyl acetate as yellow oil: 10 g (yield: 93%, 95% ee by HPLC using a chiral column)

EXAMPLE 11

(R)-4-Hydroxy-2-(3-Methoxybenzyl)cyclopent-2-enone

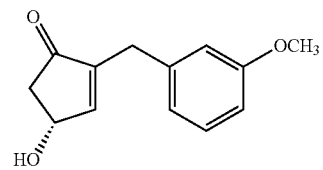 [SMILES: COc1cccc(CC2=C[C@H](O)CC2=O)c1]

(R)-3-(3-Methoxybenzyl)-4-oxocyclopent-2-enyl acetate (0.1 g, 0.38 mmol) was added to KH$_2$PO$_4$—H$_3$PO$_4$ buffer (1 ml). The mixture was added thereto Lipase derived from Pseudomonas cepacia, and 1N NaOH was slowly added to the solution at room temperature to keep the pH=7~7.5. After 3 hours, about 10% of (R)-3-(3-methoxybenzyl)-4-oxocyclopent-2-enyl acetate remained. The reaction mixture was filtered to remove Lipase and the filtrate was extracted with EtOAc, dried over MgSO$_4$, and evaporated. The resulting residue was purified by chromatography on a silica gel column using hexane-EtOAc as eluent to give the (R)-4-hy-

EXAMPLE 12

(R)-4-Hydroxy-2-(3-Methoxybenzyl)cyclopent-2-enone

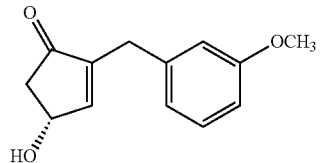 [SMILES: COc1cccc(CC2=C[C@H](O)CC2=O)c1]

(R)-3-(3-Methoxybenzyl)-4-oxocyclopent-2-enyl acetate (0.1 g, 0.38 mmol) was dissolved in THF (1 ml), 3N HCl (5 ml) was added to the solution, and the mixture was stirred at room temperature overnight. The reaction was quenched with saturated NaHCO₃ to pH=6.9 and extracted with EtOAc and the organic layer was washed with brine, dried over MgSO₄, and evaporated. The resulting residue was purified by chromatography on a silica gel column using hexane-EtOAc as eluent to give the (R)-4-hydroxy-2-(3-methoxybenzyl)cyclopent-2-enone as yellow oil: 71 mg (yield: 85%)

EXAMPLE 13

(R)-3-(3-Benzyloxybenzyl)-4-oxocyclopent-2-enyl acetate

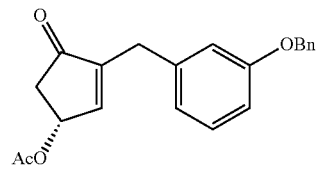 [SMILES: CC(=O)O[C@H]1C=C(Cc2cccc(OCc3ccccc3)c2)C(=O)C1]

4-Hydroxy-2-(3-Benzyloxybenzyl)cyclopent-2-enone (5.73 g, 19.48 mmol) was dissolved in isobutyl methyl ketone (60 mL), and vinyl acetate (11.2 g, 13.01 mmol) and Lipase derived from *Alculigenese* spp (0.6 g) was added to the solution, and the mixture was stirred at room temperature for 1 day. The reaction mixture was filtered to remove Lipase and the filtrate was evaporated. The resulting residue was purified by chromatography on a silica gel column using hexane-EtOAc as eluent to give the (R)-3-(3-benzyloxybenzyl)-4-oxocyclopent-2-enyl acetate as yellow oil: 2.51 g (yield: 38%, 96% ee by HPLC using a chiral column) and (S)-4-hydroxy-2-(3-(benzyloxy)benzyl)cyclopent-2-enone as yellow oil: 2.68 g (yield: 47%, >99% ee by HPLC using a chiral column)

droxy-2-(3-methoxybenzyl)cyclopent-2-enone as yellow oil: 58 mg (yield: 70%, >99.5% ee by HPLC using a chiral column)

EXAMPLE 14

(R)-3-(3-Benzyloxybenzyl)-4-oxocyclopent-2-enyl acetate

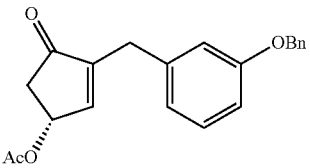 [SMILES: CC(=O)O[C@H]1C=C(Cc2cccc(OCc3ccccc3)c2)C(=O)C1]

4-Hydroxy-2-(3-Benzyloxybenzyl)cyclopent-2-enone (2.1 kg, 7.14 mol) was dissolved in isobutyl methyl ketone (21 L), and vinyl acetate (4.2 kg, 51.16 mol) and Lipase derived from *Pseudomonas cepacia* (210 g) was added to the solution, and the mixture was stirred at room temperature for 1 day. The reaction mixture was filtered to remove Lipase and the filtrate was evaporated. The resulting residue was dissolved in PhCH₃ (20 L), and triphenylphosphine (625 g, 2.38 mol) and AcOH (145 g, 2.41 mol) was added to the solution. Then diisopropylazodicarboxylate (413 g, 2.04 mol) was added to the mixture at 5° C. After the reaction was completed, the reaction mixture was filtered to remove the precipitate and the filtrate was evaporated. The residue was dissolved in EtOAc (5 L) and hexane (5 L) was added. The mixture was stirred at room t temperature overnight. The mixture was filtered to remove the precipitate and the filtrate was evaporated. The residue was purified by chromatography on a silica gel column using hexane-EtOAc as eluent to give the (R)-3-(3-benzyloxybenzyl)-4-oxocyclopent-2-enyl acetate as yellow oil: 1.8 kg (yield: 75%, 97% ee by HPLC using a chiral column)

¹H NMR (300 MHz, CDCl₃) δ 2.07 (3H, s), 2.39 (1H, dd, J=2.1, 18.8 Hz), 2.89 (1H, dd, J=6.3, 18.9), 3.49 (2H, m), 5.06 (2H, s), 5.72 (1H, m), 6.79-6.88 (3H, m), 6.98 (1H, m), 7.21-7.45 (6H, m)

EXAMPLE 15

(R)-4-Hydroxy-2-(3-benzyloxybenzyl)cyclopent-2-enone

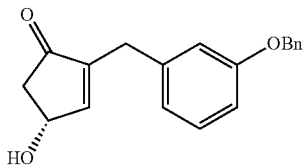 [SMILES: O=C1C[C@@H](O)C=C1Cc1cccc(OCc2ccccc2)c1]

(R)-3-(3-Benzyloxybenzyl)-4-oxocyclopent-2-enyl acetate (1.8 kg, 5.35 mol) was added to KH₂PO₄—H₃PO₄ buffer solution (20 L). The mixture was added Lipase derived from *Pseudomonas cepacia* and 1N NaOH was slowly added to the solution at room temperature to keep the ph=7~7.5. After 8 hours, (R)-3-(3-Benzyloxybenzyl)-4-oxocyclopent-2-enyl acetate remained about 10%, The reaction mixture was filtered to remove Lipase and the filtrate was extracted with EtOAc, dried over MgSO₄, and evaporated. The resulting residue was purified by chromatography on a silica gel column using hexane-EtOAc as eluent to give the (R)-4-hydroxy-2-(3-benzyloxybenzyl)cyclopent-2-enone as yellow oil: 1.3 kg (yield: 83%, >99% ee by HPLC using a chiral column)

EXAMPLE 16

(R)-4-Hydroxy-2-(3-Methoxybenzyl)cyclopent-2-enone

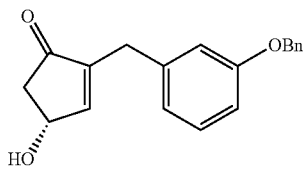

(R)-3-(3-Methoxybenzyl)-4-oxocyclopent-2-enyl acetate (0.5 g, 1.48 mmol), was dissolved in MeOH (5 ml), 7% KOH/CH$_3$OH (5 ml) was added to the solution, and the mixture was stirred at room temperature overnight. The mixture was evaporated and the resulting residue was neutralized by HCl to pH=6.5, and extracted with EtOAc. The organic layer was washed with brine, dried over MgSO$_4$, and evaporated. The resulting residue was purified by chromatography on a silica gel column using hexane-EtOAc as eluent to give (R)-4-hydroxy-2-(3-methoxybenzyl)cyclopent-2-enone as yellow oil: 0.4 g, (yield: 92%) [α]$_D^{20}$=+3.5~5.7°

EXAMPLE 17

(R)-2-(3-tert-Buthyldimethylsiloxybenzyl)-4-tetrahydrofuranyloxycyclopent-2-enone

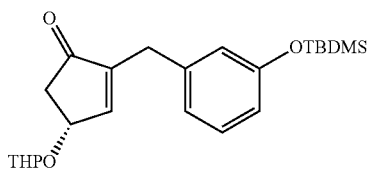

(R)-2-(3-(benzyloxy)benzyl)-4-hydroxycyclopent-2-enone (0.5 g, 1.7 mmol) and dihydropyrane (0.34 g, 4 mmol) was dissolved in CH$_2$Cl$_2$ (5 ml), p-toluenesulfonic acid (0.2 g) was added to the solution at 10° C., and the mixture was stirred at room temperature overnight. After the reaction was completed, the mixture was washed with sat. NaHCO$_3$ aq., dried over MgSO$_4$, and evaporated. The resulting residue was dissolved in EtOH (5 ml) under hydrogen, Pd/C (0.15 g) was added to the solution and the mixture was stirred at room temperature for 2 hrs. After the reaction was completed, the reaction mixture was filtered to remove the Pd/C and the filtrate was evaporated. The resulting residue was dissolved in EtOAc (5 ml), imidazole (0.24 g, 3.5 mmol) and tert-butyldimethylsilyl chloride (0.38 g, 2.55 mmol) was added to the solution and the mixture was stirred at 50° C. for 4 hrs. After the reaction was completed, the reaction mixture was filtered to remove the precipitate and washed with NaHCO$_3$ and extracted with EtOAc. The organic layer was dried over MgSO$_4$, and evaporated. The residue was purified by chromatography on a silica gel column using hexane-EtOAc as eluent to give (4R)-2-(3-(tert-butyldimethylsilyloxy)benzyl)-4-(tetrahydro-2H-pyran-2-yloxy)cyclopent-2-e none as yellow oil: 0.47 g, (yield: 69%,)

$^1$H NMR (CDCl$_3$, 500 MHz) δ 0.18 (6H, s), 0.97 (9H, s), 1.51 (4H, m), 1.75 (3H, m), 2.32 (3H, m), 2.28 (2H, m), 2.60 (1H, m), 3.12 (1H, m), 3.48 (1H, m), 3.83 (1H, m), 4.37 (1H, sept, J=7.0 Hz), 4.66 (1H, m), 6.66 (2H, m), 6.74 (1H, m), 7.12 (1H, t, J=7.5 Hz)

$^{13}$C NMR (CDCl$_3$, 500 MHz) δ −4.46, 18.16 (18.12), 19.33 (19.43), 25.29 (25.31), 25.63, 30.72 (30.77), 34.34, 35.64 (35.89), 44.73 (46.26), 49.88 (50.36), 62.37 (62.50), 71.56 (72.07), 97.33 (97.53), 117.88 (117.93), 120.64 (120.70), 121.85 (121.88), 129.28 (129.32), 141.09 (141.12), 155.62 (155.65), 216.14 (216.55)

We claim:
1. A process for preparing a racemic cyclopentenone of Formula I

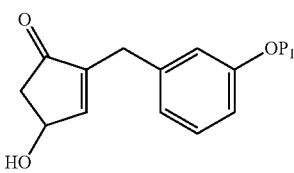

wherein P$_1$ a protecting group for the phenol group, comprising the steps of:
(a) reacting furan with an acyl donor of the acid compound of Formula V

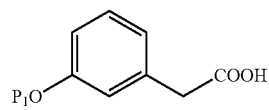

to form a 2-acylfuran of Formula IV

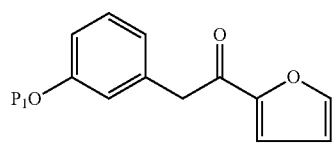

(b) reacting the 2-acylfuran of Formula IV with a reducing agent to form the corresponding furancarbinol compound of formula III:

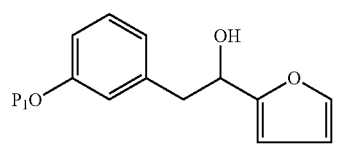

and
(c) subjecting the furancarbinol compound of formula III to a rearrangement and isomerization to form the racemic compound of Formula I.
2. The process according to claim 1, wherein P$_1$ is a C$_{1-8}$ alkyl, allyl, unsubstituted or substituted benzyl, acetyl, C$_{1-8}$ alkylcarbonyl, methoxymethyl, methoxythiomethyl, 2-methoxyethoxymethyl, bis(2-chloroethoxy)methyl, tetrahydropyranyl, tetrahydrothiopyranyl, 4-methoxytetrahydropyranyl, 4-methoxytetrahydrothiopyranyl, tetrahydrofuranyl, tetrahydrothiofuranyl, 1-ethoxyethyl, 1-methyl-1-methoxyethyl, triphenylmethyl, and $SiR_aR_bR_c$ wherein $R_a$, $R_b$ and $R_c$ are each independently a $C_{1-8}$ alkyl, phenyl, benzyl, a substituted phenyl, or a substituted benzyl.

3. The process according to claim 2, wherein $P_1$ is a $C_{1-8}$ alkyl, allyl, or an unsubstituted or substituted benzyl.

4. The process according to claim 1, wherein the acyl donor is selected from the group consisting of chloroacetic anhydride or trifluoroacetic anhydride or a mixture thereof.

5. The process according to claim 1, wherein the reducing agent is selected from the group consisting of $NaBH_4$, $LiBH_4$, $LiAlH_4$, or $(iso-Bu)_2AlH$ or a mixture thereof.

6. A process for preparing a compound of Formula I enriched in the (R)-enantiomer and having an optical purity of at least 95% enantiomeric excess,

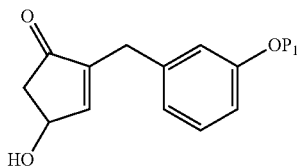

wherein $P_1$ is as defined in claim 1, comprising the steps of:
(e) enantioselectively (R)-esterifying the racemic alcohol mixture of the compound of Formula I with an acyl donor of Formula D

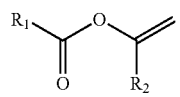

wherein $R_1$ and $R_2$ are independently a $C_{1-6}$ alkyl or H, and a first lipase;
(f) removing the unreacted (S)-alcohol; and
(g) deacylating the resultant (R)-ester.

7. The process according to claim 6, wherein the acyl donor of Formula D is vinyl acetate, isopropenyl acetate, vinyl valerate, isopropenyl valerate, vinyl butyrate, or isopropenyl butyrate or a mixture thereof.

8. The process according to claim 6, wherein the first lipase is derived from *Candida antarcitica, Achromobacter* spp., *Alcaligenese* spp., *Pseudomonas fluorescens, Pseudomonas stutzri*, or *Pseudomonas cepacia*.

9. The process according to claim 6, wherein the deacylation step (g) comprises an enzymatic cleavage reaction using a second lipase derived from *Candida antarcitica, Psudomonas* spp. or *Achromobacter* spp or a mixture thereof.

10. The process according to claim 9, wherein the second lipase is derived from *Candida antarcitica*.

11. The process according to claim 6, wherein the deacylation step (g) is a chemical hydrolysis.

12. The process according to claim 6, wherein step (t) comprises converting the unreacted (S)-alcohol into a corresponding (R)-ester by reacting the (S)-alcohol with an acyloxy donor of Formula $R_3COOH$, wherein $R_3$ is as defined in claim 5 for $R_1$ in the presence of a dialkylazodicarboxylate and a triarylphosphine.

13. The process according to claim 12, wherein the dialkylazodicarboxylate is diethylazodicarboxylate, diisopropylazodicarboxylate, or dibenzylazodicarboxylate or a mixture thereof.

14. The process according to claim 12, wherein the triarylphosphine is triphenylphosphine.

15. A racemic or an optically active compound of Formula I:

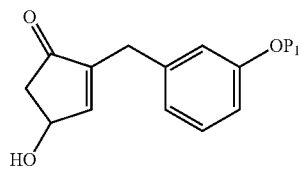

wherein $P_1$ is a protecting group for the phenol selected from the group consisting of a $C_{1-8}$ alkyl, allyl, unsubstituted or substituted benzyl, acetyl, $C_{1-8}$ alkylcarbonyl, methoxymethyl, methoxythiomethyl, 2-methoxyethoxymethyl, bis(2-chloroethoxy)methyl, tetrahydropyranyl, tetrahydrothiopyranyl, 4-methoxytetrahydropyranyl, 4-methoxytetrahydrothiopyranyl, tetrahydrofuranyl, tetrahydrothiofuranyl, 1-ethoxyethyl, 1-methyl-1-methoxyethyl, triphenylmethyl, and $SiRR_aR_bR_c$ wherein $R_a$, $R_b$ and $R_c$ are each independently a $C_{1-8}$ alkyl, phenyl, benzyl, a substituted phenyl, or a substituted benzyl.

16. A compound according to claim 15, wherein $P_1$ is benzyl or a substituted benzyl.

17. A compound according to claim 15, wherein $P_1$ is $SiR_aR_bR_c$ wherein $R_a$, $R_b$ and $R_c$ are each independently a $C_{1-8}$ alkyl, phenyl, benzyl, a substituted phenyl, or a substituted benzyl.

18. A compound according to claim 17, wherein $R_a$, $R_b$ and $R_c$ are each independently a $C_{1-8}$ alkyl.

19. A compound according to claim 15, wherein $P_1$ is a $C_{1-8}$ alkyl.

20. A compound according to claim 15, wherein $P_1$ is acetyl or a $C_{1-8}$ alkylcarbonyl.

21. A compound according to claim 15 enriched in the (R)-enantiomer and having an optical purity of at least 95% enantiomeric excess.

22. A compound according to claim 15 enriched in the (R)-enantiomer and having an optical purity of at least 99% enantiomeric excess.

23. A compound according to claim 15 enriched in the (R)-enantiomer and having an optical purity of at least 99.9% enantiomeric excess.

* * * * *